(12) United States Patent
Delli-Santi et al.

(10) Patent No.: US 8,449,612 B2
(45) Date of Patent: May 28, 2013

(54) GRAFT PULLEY AND METHODS OF USE

(75) Inventors: George Delli-Santi, Austin, TX (US); Alan W. Wolf, Kodiak, AK (US)

(73) Assignee: ArthroCare Corporation, Austin, TX (US)

( * ) Notice: Subject to any disclaimer, the term of this patent is extended or adjusted under 35 U.S.C. 154(b) by 515 days.

(21) Appl. No.: 12/619,167

(22) Filed: Nov. 16, 2009

(65) Prior Publication Data
US 2011/0118837 A1 May 19, 2011

(51) Int. Cl.
*A61F 2/08* (2006.01)
(52) U.S. Cl.
USPC ........................................ 623/13.13
(58) Field of Classification Search
USPC ............ 623/13.11–13.2, 11.11, 23.48, 17.11, 623/14.12; 606/232, 233, 228, 222, 224, 606/148, 151, 138–144
See application file for complete search history.

(56) References Cited

U.S. PATENT DOCUMENTS

| | | | |
|---|---|---|---|
| 3,896,500 A | 7/1975 | Rambert et al. | 623/13.14 |
| 3,973,277 A | 8/1976 | Semple et al. | 623/13.14 |
| 4,126,165 A | 11/1978 | Guignard et al. | 142/56 |
| 4,149,277 A | 4/1979 | Bokros | 623/13.2 |
| 4,187,558 A | 2/1980 | Dahlen et al. | 623/13.14 |
| 4,204,544 A | 5/1980 | Feldstein et al. | 600/375 |
| 4,275,717 A | 6/1981 | Bolesky | 606/63 |
| 4,309,778 A | 1/1982 | Buechel et al. | 623/20.29 |
| 4,708,132 A | 11/1987 | Silvestrini | 606/66 |
| 4,712,542 A | 12/1987 | Daniel et al. | 606/96 |
| 4,776,851 A | 10/1988 | Bruchman et al. | 623/13.11 |
| 4,870,957 A | 10/1989 | Goble et al. | 623/13.12 |
| 4,950,270 A | 8/1990 | Bowman et al. | 606/72 |
| 4,997,433 A | 3/1991 | Goble et al. | 606/64 |

(Continued)

FOREIGN PATENT DOCUMENTS

| | | |
|---|---|---|
| DE | 9002844 | 1/1991 |
| DE | 29607352 | 9/1996 |

(Continued)

OTHER PUBLICATIONS

Smith & Nephew, "Arthroscopic Repair of a Bankart Lesion Using TAG Suture Anchors," 12 pgs, May 1996.

(Continued)

*Primary Examiner* — Alvin Stewart
(74) *Attorney, Agent, or Firm* — Matthew Scheele; Briran Szymczak (57) ABSTRACT

A placement assembly used for positioning and holding a ligament graft within a selected bone tunnel. The assembly includes a graft pulley, a surgical suture, and a graft pulley placement instrument. The graft pulley includes a pulley portion and a bone anchoring portion. The pulley portion is adapted to receive the surgical suture and for surgical suture to be drawn through it, to act as a pulley. The bone anchoring portion comprises at least one flexible wing that is adapted to selectively fix the graft pulley within a bone tunnel. At least one wing is adapted to flex during insertion into a bone tunnel and then resist flex and thereby resist movement back out of the tunnel and hence wedge itself within the tunnel. The graft instrument may be selectively attached to the graft pulley and includes a handle and elongate body, adapted to insert the graft pulley into the selected bone tunnel. Once the graft pulley is in place, the placement instrument may then be detached and withdrawn leaving the graft pulley firmly fixed within the bone tunnel and can then be used to position a ligament graft.

20 Claims, 8 Drawing Sheets

U.S. PATENT DOCUMENTS

| | | | | |
|---|---|---|---|---|
| 5,037,422 A * | 8/1991 | Hayhurst et al. | | 606/232 |
| 5,037,426 A | 8/1991 | Goble et al. | | 606/96 |
| 5,046,513 A | 9/1991 | Gatturna et al. | | 128/898 |
| 5,080,680 A * | 1/1992 | Mikhail et al. | | 623/23.37 |
| 5,100,417 A * | 3/1992 | Cerier et al. | | 606/139 |
| 5,112,338 A | 5/1992 | Anspach, III | | 606/99 |
| 5,139,520 A | 8/1992 | Rosenberg | | 606/87 |
| 5,147,361 A | 9/1992 | Ojima et al. | | 606/61 |
| 5,151,104 A | 9/1992 | Kenna | | 606/328 |
| D330,591 S | 10/1992 | Rosenberg et al. | | D24/147 |
| 5,152,790 A | 10/1992 | Rosenberg et al. | | 623/13.14 |
| 5,156,616 A | 10/1992 | Meadows et al. | | 606/232 |
| 5,176,682 A | 1/1993 | Chow | | 606/72 |
| 5,203,787 A | 4/1993 | Noblitt et al. | | 606/232 |
| 5,207,679 A | 5/1993 | Li | | 606/232 |
| 5,224,946 A * | 7/1993 | Hayhurst et al. | | 606/232 |
| 5,258,003 A | 11/1993 | Ciaglia et al. | | 606/185 |
| 5,258,016 A | 11/1993 | DiPoto et al. | | 606/232 |
| 5,266,075 A | 11/1993 | Clark et al. | | 606/138 |
| 5,306,301 A | 4/1994 | Graf et al. | | 623/13 |
| 5,324,308 A | 6/1994 | Pierce | | 606/232 |
| 5,330,468 A | 7/1994 | Burkhart | | 606/96 |
| 5,350,380 A | 9/1994 | Goble et al. | | 606/80 |
| 5,350,383 A | 9/1994 | Schmieding et al. | | 606/96 |
| 5,356,413 A * | 10/1994 | Martins et al. | | 606/75 |
| 5,364,400 A | 11/1994 | Rego, Jr. et al. | | 606/72 |
| 5,370,662 A | 12/1994 | Stone et al. | | 606/232 |
| 5,383,932 A * | 1/1995 | Wilson et al. | | 623/23.48 |
| RE34,871 E | 3/1995 | McGuire et al. | | 606/73 |
| 5,405,359 A | 4/1995 | Pierce | | 606/232 |
| 5,423,860 A * | 6/1995 | Lizardi et al. | | 606/232 |
| 5,443,482 A | 8/1995 | Stone et al. | | 606/232 |
| 5,464,427 A * | 11/1995 | Curtis et al. | | 606/232 |
| 5,472,452 A | 12/1995 | Trott | | 606/232 |
| 5,480,403 A * | 1/1996 | Lee et al. | | 606/232 |
| 5,486,197 A * | 1/1996 | Le et al. | | 606/232 |
| 5,505,735 A | 4/1996 | Li | | 623/13.14 |
| 5,522,843 A * | 6/1996 | Zang | | 606/232 |
| 5,534,011 A | 7/1996 | Greene, Jr. et al. | | 606/232 |
| 5,545,180 A * | 8/1996 | Le et al. | | 606/232 |
| 5,554,192 A * | 9/1996 | Crowninshield | | 623/23.48 |
| 5,556,411 A | 9/1996 | Taoda et al. | | 606/185 |
| 5,591,190 A | 1/1997 | Yoon | | 606/185 |
| 5,591,232 A | 1/1997 | Rahimi et al. | | 128/898 |
| 5,601,557 A * | 2/1997 | Hayhurst | | 606/232 |
| 5,601,562 A | 2/1997 | Wolf et al. | | 606/86 |
| 5,609,634 A | 3/1997 | Voydeville | | 623/13.11 |
| 5,618,314 A * | 4/1997 | Harwin et al. | | 606/232 |
| 5,632,748 A * | 5/1997 | Beck et al. | | 606/89 |
| 5,643,266 A | 7/1997 | Li | | 623/13.13 |
| 5,643,321 A * | 7/1997 | McDevitt | | 606/232 |
| 5,645,588 A | 7/1997 | Graf et al. | | 606/151 |
| 5,647,874 A | 7/1997 | Hayhurst | | 606/72 |
| 5,658,289 A | 8/1997 | Boucher et al. | | 623/13.14 |
| 5,662,654 A * | 9/1997 | Thompson | | 606/232 |
| 5,674,224 A | 10/1997 | Howell et al. | | 606/88 |
| 5,683,471 A | 11/1997 | Incavo et al. | | 128/898 |
| 5,690,676 A * | 11/1997 | DiPoto et al. | | 606/232 |
| 5,702,422 A | 12/1997 | Stone | | 606/232 |
| 5,707,395 A * | 1/1998 | Li | | 606/232 |
| 5,713,897 A | 2/1998 | Goble et al. | | 606/53 |
| 5,720,766 A * | 2/1998 | Zang et al. | | 606/232 |
| 5,725,529 A * | 3/1998 | Nicholson et al. | | 606/232 |
| 5,725,541 A | 3/1998 | Anspach et al. | | 606/151 |
| 5,733,307 A | 3/1998 | Dinsdale | | 606/232 |
| 5,735,867 A | 4/1998 | Golser et al. | | 606/185 |
| 5,766,178 A * | 6/1998 | Michielli et al. | | 606/95 |
| 5,766,250 A | 6/1998 | Chervitz et al. | | 606/232 |
| 5,769,894 A | 6/1998 | Ferragamo | | 606/148 |
| 5,782,749 A | 7/1998 | Riza | | 600/117 |
| 5,782,917 A * | 7/1998 | Carn | | 623/23.48 |
| 5,791,350 A | 8/1998 | Morton | | 600/590 |
| 5,797,963 A | 8/1998 | McDevitt | | 606/232 |
| 5,813,808 A * | 9/1998 | Wu | | 411/32 |
| 5,814,070 A | 9/1998 | Borzone et al. | | 606/232 |
| 5,824,011 A | 10/1998 | Stone et al. | | 606/232 |
| 5,840,078 A * | 11/1998 | Yerys | | 606/151 |
| 5,849,004 A * | 12/1998 | Bramlet | | 606/232 |
| 5,861,043 A * | 1/1999 | Carn | | 623/23.48 |
| 5,868,789 A | 2/1999 | Huebner | | 606/232 |
| 5,871,504 A | 2/1999 | Eaton et al. | | 606/232 |
| 5,879,403 A * | 3/1999 | Ostiguy et al. | | 623/23.48 |
| 5,891,150 A | 4/1999 | Chan | | 606/96 |
| 5,891,168 A | 4/1999 | Thai | | 606/232 |
| 5,895,425 A | 4/1999 | Grafton et al. | | 606/73 |
| 5,913,860 A | 6/1999 | Scholl | | 606/100 |
| 5,918,604 A | 7/1999 | Whelan | | 128/898 |
| RE36,289 E * | 8/1999 | Le et al. | | 606/232 |
| 5,935,129 A * | 8/1999 | McDevitt et al. | | 606/232 |
| 5,935,169 A * | 8/1999 | Chan | | 623/23.48 |
| 5,957,953 A * | 9/1999 | DiPoto et al. | | 606/232 |
| 5,964,783 A | 10/1999 | Grafton et al. | | 606/232 |
| 5,972,034 A * | 10/1999 | Hofmann et al. | | 623/23.48 |
| 5,984,966 A | 11/1999 | Kiema et al. | | 623/13.14 |
| 5,989,253 A | 11/1999 | Bigliardi | | 606/72 |
| 6,022,373 A * | 2/2000 | Li | | 606/232 |
| 6,045,573 A | 4/2000 | Wenstrom, Jr. et al. | | 606/232 |
| 6,056,752 A | 5/2000 | Roger | | 623/13.12 |
| 6,068,648 A | 5/2000 | Cole et al. | | 606/232 |
| D426,305 S | 6/2000 | Hein | | D24/147 |
| 6,080,154 A | 6/2000 | Reay-Young et al. | | 606/60 |
| 6,086,591 A | 7/2000 | Bojarski | | 606/64 |
| 6,099,568 A | 8/2000 | Simonian et al. | | 623/13.11 |
| 6,110,207 A | 8/2000 | Eichhorn et al. | | 623/13.14 |
| 6,117,161 A | 9/2000 | Li et al. | | 606/232 |
| 6,129,762 A * | 10/2000 | Li | | 623/13.11 |
| 6,132,433 A | 10/2000 | Whelan | | 606/72 |
| 6,146,406 A * | 11/2000 | Shluzas et al. | | 606/232 |
| 6,146,407 A | 11/2000 | Krebs | | 606/232 |
| 6,152,928 A * | 11/2000 | Wenstrom, Jr. | | 606/232 |
| 6,156,039 A | 12/2000 | Thai | | 606/72 |
| 6,187,011 B1 | 2/2001 | Torrie | | 606/96 |
| 6,214,007 B1 | 4/2001 | Anderson | | 606/73 |
| 6,221,107 B1 | 4/2001 | Steiner et al. | | 623/13.14 |
| 6,224,603 B1 | 5/2001 | Marino | | 606/79 |
| 6,235,057 B1 | 5/2001 | Roger et al. | | 623/13.12 |
| 6,264,677 B1 | 7/2001 | Simon et al. | | 606/232 |
| 6,280,477 B1 * | 8/2001 | Mastrorio et al. | | 623/23.48 |
| 6,283,973 B1 | 9/2001 | Hubbard et al. | | 606/104 |
| 6,283,996 B1 | 9/2001 | Chervitz et al. | | 623/13.14 |
| 6,306,138 B1 | 10/2001 | Clark et al. | | 606/65 |
| 6,319,270 B1 | 11/2001 | Grafton et al. | | 606/232 |
| 6,328,758 B1 | 12/2001 | Tornier et al. | | 606/232 |
| 6,355,053 B1 | 3/2002 | Li | | 606/232 |
| 6,355,066 B1 * | 3/2002 | Kim | | 623/13.14 |
| 6,365,149 B2 | 4/2002 | Vyakarnam et al. | | 424/93.1 |
| 6,371,124 B1 | 4/2002 | Whelan | | 128/898 |
| 6,379,361 B1 | 4/2002 | Beck, Jr. et al. | | 606/72 |
| 6,402,757 B1 | 6/2002 | Moore, III et al. | | 606/80 |
| 6,440,134 B1 * | 8/2002 | Zaccherotti et al. | | 606/62 |
| 6,491,714 B1 | 12/2002 | Bennett | | 606/232 |
| 6,499,486 B1 | 12/2002 | Chervitz et al. | | 128/898 |
| 6,508,830 B2 * | 1/2003 | Steiner | | 606/232 |
| 6,517,542 B1 | 2/2003 | Papay et al. | | 606/232 |
| 6,517,578 B2 | 2/2003 | Hein | | 623/13.13 |
| 6,527,795 B1 | 3/2003 | Lizardi | | 606/232 |
| 6,533,802 B2 | 3/2003 | Bojarski et al. | | 606/232 |
| 6,533,816 B2 | 3/2003 | Sklar | | 623/13.14 |
| 6,540,783 B1 | 4/2003 | Whittaker et al. | | 623/13.14 |
| 6,544,273 B1 * | 4/2003 | Harari et al. | | 606/151 |
| 6,547,800 B2 | 4/2003 | Foerster et al. | | 606/151 |
| 6,551,343 B1 | 4/2003 | Tormala et al. | | 606/213 |
| 6,554,553 B2 | 4/2003 | Freedland | | 411/392 |
| 6,554,862 B2 * | 4/2003 | Hays et al. | | 623/13.14 |
| 6,562,071 B2 | 5/2003 | Jarvinen | | 623/13.14 |
| 6,579,295 B1 | 6/2003 | Supinski | | 623/13.14 |
| 6,589,245 B1 | 7/2003 | Weiler et al. | | 623/13.14 |
| 6,599,289 B1 | 7/2003 | Bojarski et al. | | 606/60 |
| 6,610,064 B1 | 8/2003 | Goble et al. | | 606/72 |
| 6,610,080 B2 | 8/2003 | Morgan | | 606/232 |
| 6,616,694 B1 | 9/2003 | Hart | | 623/13.14 |
| 6,623,524 B2 | 9/2003 | Schmieding | | 623/13.14 |
| 6,629,977 B1 | 10/2003 | Wolf | | 606/99 |
| 6,632,245 B2 | 10/2003 | Kim | | 623/13.14 |
| 6,635,058 B2 | 10/2003 | Beyar et al. | | 606/232 |
| 6,635,074 B2 | 10/2003 | Bartlett | | 606/232 |
| 6,652,560 B1 | 11/2003 | Gerke et al. | | 606/232 |

| Patent/Pub No. | Date | Inventor | Class |
|---|---|---|---|
| 6,652,563 B2 * | 11/2003 | Dreyfuss | 606/232 |
| 6,663,656 B2 | 12/2003 | Schmieding et al. | 606/232 |
| 6,685,728 B2 | 2/2004 | Sinnott et al. | 606/232 |
| 6,689,153 B1 | 2/2004 | Skiba | 606/232 |
| 6,736,847 B2 | 5/2004 | Seyr et al. | 623/13.14 |
| 6,752,833 B2 * | 6/2004 | Hesseling et al. | 623/23.48 |
| 6,780,187 B2 | 8/2004 | Supinski | 623/13.14 |
| 6,780,188 B2 | 8/2004 | Clark et al. | 606/73 |
| 6,802,862 B1 | 10/2004 | Roger et al. | 623/13.14 |
| 6,808,528 B2 | 10/2004 | Justin | 606/72 |
| 6,833,005 B1 * | 12/2004 | Mantas et al. | 623/13.13 |
| 6,860,887 B1 | 3/2005 | Frankle et al. | 606/104 |
| 6,875,214 B2 | 4/2005 | Supinski | 623/13.14 |
| 6,878,166 B2 | 4/2005 | Clark et al. | 623/13.12 |
| 6,887,271 B2 | 5/2005 | Justin et al. | 623/13.14 |
| 6,890,354 B2 | 5/2005 | Steiner et al. | 623/13.14 |
| 6,905,513 B1 | 6/2005 | Metzger | 623/20.17 |
| 6,932,834 B2 * | 8/2005 | Lizardi et al. | 606/232 |
| 6,994,725 B1 * | 2/2006 | Goble | 623/13.14 |
| 7,001,429 B2 | 2/2006 | Ferguson | 623/13.14 |
| 7,056,340 B2 | 6/2006 | McKernan et al. | 623/13.12 |
| 7,063,717 B2 | 6/2006 | St. Pierre et al. | 606/232 |
| 7,063,724 B2 | 6/2006 | Re et al. | 623/13.14 |
| 7,083,647 B1 * | 8/2006 | Sklar et al. | 623/13.14 |
| 7,137,996 B2 | 11/2006 | Steiner et al. | 623/13.14 |
| 7,144,413 B2 | 12/2006 | Wilford et al. | 606/232 |
| 7,172,595 B1 | 2/2007 | Goble | 606/86 A |
| 7,175,632 B2 | 2/2007 | Singhatat et al. | 606/72 |
| 7,226,469 B2 | 6/2007 | Benavitz et al. | 606/232 |
| D547,451 S | 7/2007 | Asfora | D24/146 |
| 7,285,121 B2 | 10/2007 | Braun et al. | 606/279 |
| 7,322,986 B2 | 1/2008 | Wolf | 606/304 |
| 7,338,492 B2 | 3/2008 | Singhatat et al. | 606/232 |
| 7,468,074 B2 | 12/2008 | Caborn et al. | 623/13.14 |
| 7,485,136 B2 | 2/2009 | Chan | 606/321 |
| 7,588,586 B2 | 9/2009 | Whittaker | 606/232 |
| 7,591,850 B2 | 9/2009 | Cavazzoni | 623/13.11 |
| 7,594,929 B2 | 9/2009 | Collette | 623/13.14 |
| 7,637,910 B2 | 12/2009 | Schmieding et al. | 606/80 |
| 7,637,949 B2 | 12/2009 | Hart | 623/13.14 |
| 7,645,293 B2 * | 1/2010 | Martinek et al. | 606/232 |
| 7,674,275 B2 * | 3/2010 | Martin et al. | 606/232 |
| 7,686,838 B2 | 3/2010 | Wolf et al. | 623/13.11 |
| 7,713,293 B2 | 5/2010 | Tucciarone et al. | 606/321 |
| 7,766,964 B2 | 8/2010 | Stone et al. | 623/13.13 |
| 7,780,701 B1 * | 8/2010 | Meridew et al. | 606/232 |
| 7,896,901 B2 | 3/2011 | Whittaker | 606/232 |
| 7,951,198 B2 | 5/2011 | Sucec et al. | 623/13.11 |
| 8,029,537 B2 * | 10/2011 | West et al. | 606/232 |
| 8,034,090 B2 | 10/2011 | Stone et al. | 606/321 |
| 8,043,347 B2 | 10/2011 | Jiang et al. | 606/311 |
| 8,043,374 B2 | 10/2011 | Re et al. | 623/13.14 |
| 8,062,363 B2 | 11/2011 | Hirpara et al. | 623/13.14 |
| 8,092,528 B2 * | 1/2012 | Pellegrino et al. | 623/13.14 |
| 8,100,968 B2 | 1/2012 | Chan | 623/13.14 |
| 8,100,969 B2 | 1/2012 | Hart | 623/13.14 |
| 8,110,001 B2 | 2/2012 | Carter et al. | 623/13.14 |
| 8,114,127 B2 * | 2/2012 | West, Jr. | 606/232 |
| 8,114,129 B2 | 2/2012 | Lubbers et al. | 606/232 |
| 2001/0018619 A1 | 8/2001 | Enzerink et al. | 623/23.72 |
| 2001/0020187 A1 * | 9/2001 | Guettinger et al. | 623/23.25 |
| 2001/0021875 A1 | 9/2001 | Enzerink et al. | 623/13.17 |
| 2001/0025181 A1 | 9/2001 | Freedlan | 606/54 |
| 2002/0007182 A1 * | 1/2002 | Kim | 606/53 |
| 2002/0019635 A1 | 2/2002 | Wenstrom, Jr. et al. | 623/13.12 |
| 2002/0019670 A1 | 2/2002 | Crawley et al. | 623/11.11 |
| 2002/0038123 A1 | 3/2002 | Visotsky et al. | 606/73 |
| 2002/0040241 A1 | 4/2002 | Jarvinen | 623/13.14 |
| 2002/0111693 A1 * | 8/2002 | Hesseling et al. | 623/23.48 |
| 2002/0128721 A1 * | 9/2002 | Chan | 623/23.48 |
| 2003/0088250 A1 * | 5/2003 | Colleran et al. | 606/72 |
| 2003/0187446 A1 * | 10/2003 | Overaker et al. | 606/73 |
| 2004/0111117 A1 * | 6/2004 | Colleran et al. | 606/232 |
| 2004/0176854 A1 * | 9/2004 | Hesseling et al. | 623/23.48 |
| 2004/0193167 A1 | 9/2004 | Tucciarone et al. | 606/73 |
| 2005/0075636 A1 | 4/2005 | Gotzen | 606/72 |
| 2005/0222619 A1 | 10/2005 | Dreyfuss et al. | 606/72 |
| 2006/0030940 A1 | 2/2006 | Schmieding | 623/13.14 |
| 2006/0253119 A1 | 11/2006 | Berberich et al. | 606/72 |
| 2006/0276841 A1 * | 12/2006 | Barbieri et al. | 606/232 |
| 2007/0021751 A1 * | 1/2007 | Reay-Young et al. | 606/72 |
| 2007/0093895 A1 | 4/2007 | Donnelly et al. | 623/13.14 |
| 2007/0162124 A1 | 7/2007 | Whittaker | 623/13.14 |
| 2007/0213730 A1 | 9/2007 | Martinek et al. | 606/72 |
| 2007/0225805 A1 | 9/2007 | Schmieding | 623/13.14 |
| 2007/0260249 A1 | 11/2007 | Boyajian et al. | 606/72 |
| 2007/0260259 A1 * | 11/2007 | Fanton et al. | 606/99 |
| 2007/0270857 A1 | 11/2007 | Lombardo et al. | 606/232 |
| 2008/0154314 A1 | 6/2008 | McDevitt | 623/13.14 |
| 2008/0228271 A1 | 9/2008 | Stone et al. | 623/13.12 |
| 2008/0234819 A1 | 9/2008 | Schmieding et al. | 623/13.14 |
| 2008/0275553 A1 | 11/2008 | Wolf et al. | 623/13.14 |
| 2008/0288069 A1 * | 11/2008 | Wolf et al. | 623/13.14 |
| 2008/0300683 A1 | 12/2008 | Altman et al. | 623/13.11 |
| 2009/0018654 A1 | 1/2009 | Schmieding et al. | 623/13.14 |
| 2009/0018655 A1 | 1/2009 | Brunelle et al. | 623/13.19 |
| 2009/0030516 A1 | 1/2009 | Imbert | 623/13.14 |
| 2009/0093880 A1 | 4/2009 | Justin | 623/13.14 |
| 2009/0125058 A1 * | 5/2009 | Bodner et al. | 606/232 |
| 2009/0216326 A1 * | 8/2009 | Hirpara et al. | 623/13.14 |
| 2009/0234451 A1 | 9/2009 | Manderson | 623/13.14 |
| 2009/0248068 A1 * | 10/2009 | Lombardo et al. | 606/232 |
| 2009/0265004 A1 | 10/2009 | Morgan et al. | 623/13.14 |
| 2009/0306776 A1 | 12/2009 | Murray | 623/13.12 |
| 2009/0306777 A1 | 12/2009 | Widmer et al. | 623/13.14 |
| 2009/0318964 A1 * | 12/2009 | Lombardo et al. | 606/232 |
| 2009/0319043 A1 | 12/2009 | McDevitt | 623/13.14 |
| 2010/0004683 A1 * | 1/2010 | Hoof et al. | 606/232 |
| 2010/0016894 A1 * | 1/2010 | Houard et al. | 606/232 |
| 2010/0063541 A1 | 3/2010 | Brunelle et al. | 606/232 |
| 2010/0121448 A1 | 5/2010 | Mckernan et al. | 623/13.11 |
| 2010/0121449 A1 | 5/2010 | Sklar et al. | 623/13.14 |
| 2010/0145448 A1 * | 6/2010 | Montes De Oca Balderas et al. | 623/13.14 |
| 2010/0152850 A1 | 6/2010 | Montgomery et al. | 623/13.14 |
| 2010/0161054 A1 | 6/2010 | Park et al. | 623/13.14 |
| 2010/0217389 A1 | 8/2010 | Cheng et al. | 623/13.14 |
| 2010/0249838 A1 | 9/2010 | Stopek et al. | 606/246 |
| 2010/0249854 A1 | 9/2010 | Thomas et al. | 606/301 |
| 2010/0292792 A1 | 11/2010 | Stone et al. | 606/301 |
| 2010/0305698 A1 | 12/2010 | Metzger et al. | 623/13.12 |
| 2010/0312341 A1 | 12/2010 | Kaiser et al. | 623/13.14 |
| 2010/0324676 A1 | 12/2010 | Albertorio et al. | 623/13.14 |
| 2011/0040380 A1 | 2/2011 | Schmieding et al. | 623/13.14 |
| 2011/0046733 A1 | 2/2011 | Eggli | 623/13.14 |
| 2011/0046734 A1 | 2/2011 | Tobis et al. | 623/13.14 |
| 2011/0106253 A1 | 5/2011 | Barwood et al. | 623/13.14 |
| 2011/0112640 A1 | 5/2011 | Amis et al. | 623/13.14 |
| 2011/0112641 A1 * | 5/2011 | Justin et al. | 623/13.14 |
| 2011/0118838 A1 | 5/2011 | Delli-Santi et al. | 623/13.14 |
| 2011/0137416 A1 | 6/2011 | Myers | 623/13.14 |
| 2011/0152928 A1 * | 6/2011 | Colleran et al. | 606/232 |
| 2011/0153018 A1 | 6/2011 | Walters et al. | 623/13.14 |
| 2011/0160767 A1 | 6/2011 | Stone et al. | 606/232 |
| 2011/0184227 A1 | 7/2011 | Altman et al. | 600/37 |
| 2011/0184517 A1 | 7/2011 | Baird et al. | 623/13.14 |
| 2011/0196432 A1 | 8/2011 | Griffis, III | 606/86 R |
| 2011/0196490 A1 | 8/2011 | Gadikota et al. | 623/13.14 |
| 2011/0208305 A1 | 8/2011 | Malinin et al. | 623/13.14 |
| 2011/0218625 A1 | 9/2011 | Berelsman et al. | 623/13.14 |
| 2011/0270306 A1 | 11/2011 | Denham et al. | 606/228 |
| 2011/0282447 A1 | 11/2011 | Niu et al. | 623/13.11 |
| 2011/0282450 A1 | 11/2011 | Donnelly et al. | 623/13.14 |
| 2011/0288584 A1 | 11/2011 | Bojarski et al. | 606/232 |
| 2011/0288641 A1 | 11/2011 | Whittaker et al. | 623/13.14 |
| 2011/0301707 A1 | 12/2011 | Buskirk et al. | 623/13.14 |
| 2011/0301708 A1 | 12/2011 | Stone et al. | 623/13.14 |
| 2011/0313453 A1 * | 12/2011 | Krumme et al. | 606/232 |
| 2012/0035671 A1 | 2/2012 | Hodge et al. | 606/328 |
| 2012/0053630 A1 | 3/2012 | Denham et al. | 606/232 |

FOREIGN PATENT DOCUMENTS

| | | |
|---|---|---|
| EP | 238223 | 9/1987 |
| EP | 279129 | 8/1988 |
| EP | 317406 | 5/1989 |

| | | |
|---|---|---|
| EP | 379789 | 11/1989 |
| EP | 346469 | 12/1989 |
| EP | 574707 | 12/1993 |
| EP | 619982 | 3/1994 |
| EP | 0 674 880 | 3/1995 |
| EP | 0865774 | 9/1998 |
| EP | 1066805 | 6/2000 |
| EP | 1180351 | 2/2002 |
| FR | 2395012 | 1/1979 |
| FR | 2590792 | 6/1987 |
| FR | 2683715 | 5/1993 |
| FR | 2725615 | 4/1996 |
| FR | 2732211 | 4/1996 |
| GB | 2288739 | 11/1995 |
| GB | 2337463 | 11/1999 |
| SU | 1521465 | 11/1989 |
| WO | 93/25148 | 12/1993 |
| WO | 95/11631 | 5/1995 |
| WO | 96/29029 | 9/1996 |
| WO | 96/39934 | 12/1996 |
| WO | 97/20522 | 6/1997 |
| WO | 98/12991 | 4/1998 |
| WO | 98/12992 | 4/1998 |
| WO | 98/22048 | 5/1998 |
| WO | 98/38937 | 9/1998 |
| WO | 99/52472 | 10/1999 |
| WO | 99/59488 | 11/1999 |
| WO | 03/088874 | 10/2003 |

OTHER PUBLICATIONS

F.H. Fuh, et al., Anatomic ACL Double-Bundle Reconstruction, Orthopedic Technology Review vol. 7 No. 4, 6 pgs, 2005.

Daily Updates, "ACL Reconstruction Using a Double-Looped Semitendinous and Gracilis (DLSTG) Hamstring Graft with the Bone Much Screw and Sasherloc Device from Arthrotec", <www.ptupdate.com/members/daily/Art012602.htm>, Printed Aug. 21, 2006.

"Graft Choices in ACL Reconstruction", Carleton Sports Medicine, <www.carletonsportsmed.com/graftacl.htm>, Printed Aug. 21, 2006.

"Distal Tendon Repair with the Lubbers Technique", Ortheon Medical, <www.ortheon.com/distal.htm>, Printed Aug. 21, 2006.

UK Search Report for GB 9915550 1 pg, Jun. 13, 2000.
UK Search Report for GB 0116605 1 pg, Mar. 27, 2002.
UK Search Report for GB 0208667 1 pg, Feb. 24, 2003.
European Search Report for EP 00113471 2 pgs, Jan. 26, 2001.
European Search Report for EP 02014485 2 pgs, Nov. 4, 2003.
European Search Report for EP 98301702 2 pgs, Jun. 23, 1998.
PCT International Search Report for PCT/GB03/01606 3 pgs, Mailed Sep. 4, 2003.
PCT Notification of the International Search Report and Written Opinion for PCT/US05/17382, 11 pgs, Mailed Oct. 23, 2007.

* cited by examiner

GRAFT PULLEY AND METHODS OF USE

FIELD OF THE INVENTION

The present invention relates generally to an apparatus and method for positioning a ligament graft, and more particularly to an implantable graft pulley adapted to firmly fix within a selected bone tunnel and assist the positioning of a graft within said bone tunnel.

BACKGROUND OF THE INVENTION

One of the most common sports injuries to the knee involves a tearing or detachment of the anterior cruciate (ACL) ligament in the knee. Over the years, surgery to repair this injury has evolved from open reduction surgical procedures on the knee, to less invasive techniques. The goal of the surgery is to attach a graft ligament, between the femur and the tibia. Various grafts may be used, including bone-tendon-bone grafts, soft tissue grafts or an artificial tendon. Whichever graft is used, a typical procedure involves drilling a long tunnel from the anterior proximal end of the tibia, through the distal anterior portion of the femur.

In some procedures a button type fixation device is used, to hold or position one end of the graft in place. The button is typically located external to the knee, close to the bone tunnel exit on the femur and there are numerous disadvantages associated with this button and the button's location. Firstly, this external location is some distance from the site where the graft may be fixed within the bone tunnel, which makes positioning the graft more difficult and requires additional lengths of sutures to attach the graft to this button. The button also necessitates the extension of the bone tunnel through the femur skin and quadriceps muscle, causing additional trauma to the leg and the increased potential for infections or nerve damage. It is also considered less cosmetically desirable. This external button may also cause interference with the tourniquet used during the surgical procedure.

Several products have more recently been presented that appear to position a graft within a bone tunnel without an incision in the anterior portion of the femur. U.S. Pat. No. 7,381,213, the complete disclosure of which is incorporated herein by reference, describes a radially expanding suture anchor, including a bore formed therein. This system also includes an expander pin to cause the anchor to radially expand within a bone tunnel or hole, into the bone wall to securely attach to bone.

An externally threaded anchor and pulley is described in commonly assigned patent application entitled, "Threaded Pulley Anchor Apparatus and Methods for Use in Surgical Repair of Ligament or Tendon", application Ser. No. 11/599,138, filed Nov. 14, 2006, and a bullet-shaped anchor is described in commonly assigned patent application entitled, "External Bullet Anchor Apparatus and Method for Use in Surgical Repair of Ligament of Tendon, application Ser. No. 11/595,353, filed Nov. 9, 2006, the complete disclosures of which are incorporated herein by reference.

SUMMARY OF THE INVENTION

The present disclosure presents an improved placement assembly for positioning a ligament graft within a selected bone tunnel. The assembly includes a surgical suture which may be assembled with a graft pulley, and a graft pulley placement instrument removably connected with said graft pulley. The graft pulley has a pulley portion and a bone anchoring portion. The pulley portion includes an aperture or channel sized to receive the surgical suture, so that the surgical suture may be drawn through the aperture, to act as a pulley. The bone anchoring portion includes at least one flexible wing that is adapted to selectively fix the graft pulley within a bone tunnel. The placement instrument is adapted to place the graft pulley within the bone tunnel and also to assist in fixing it within the bone tunnel and the instrument includes a handle and elongate body. Once the graft pulley is in place, the instrument may then be detached from the graft pulley and withdrawn from the bone tunnel.

In another aspect a graft pulley is disclosed adapted for positioning a ligament graft within a selected bone tunnel. The graft pulley includes a pulley portion having an aperture or channel sized to receive surgical suture and a bone anchoring portion having at least one flexible wing, adapted to selectively fix the graft pulley within a bone tunnel.

In yet another aspect a graft pulley for positioning a ligament graft within a bone tunnel is disclosed, including a pulley portion having an aperture or channel sized to receive surgical suture and a bone anchoring portion.

In yet another aspect a method of performing a medical procedure on a body is disclosed. The method includes drilling a bone tunnel and then inserting a graft pulley into the bone tunnel. The graft pulley includes a pulley portion and a bone anchoring portion. The pulley portion has an aperture sized to receive a surgical suture and the bone anchoring portion has at least one flexible wing adapted to fix the graft anchor within a bone tunnel. At least one wing is then flexed in a second direction, so as to slide the graft pulley into the bone tunnel in a first direction, and once the graft pulley is in place the graft pulley is retracted in the second direction, to firmly fix the graft pulley within the bone tunnel.

The present disclosure includes a number of important technical advantages. One technical advantage is that the pulley may be precisely, quickly and easily slid into place. Another advantage is that the pulley may not cause any significant trauma to the bone tunnel wall during insertion as well as during fixation. Another advantage is that this invention does not require an incision in the anterior femur, reducing the trauma to the femur and likelihood of an additional wound site infection, unsightly markings of the incision site and interference with tourniquets or equipment used during surgery. Another advantage is that the graft pulley may be placed closer to where the graft may be anchored, potentially reducing the length of sutures required for the procedure, and thereby reducing the complexity of the procedure. Another advantage is that the graft may be easily positioned within the bone tunnel without extra placement equipment. Additional advantages will be apparent to those of skill in the art and from the figures, description and claims provided herein.

BRIEF DESCRIPTION OF THE DRAWINGS

The invention may best be understood by reference to the following description taken in conjunction with the accompanying drawings in which.

DETAILED DESCRIPTION

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Last, it is to be appreciated that unless defined otherwise, all technical and scientific terms used herein have the same meaning as commonly understood by one of ordinary skill in the art to which this invention belongs.

Figures 1A, 1B:
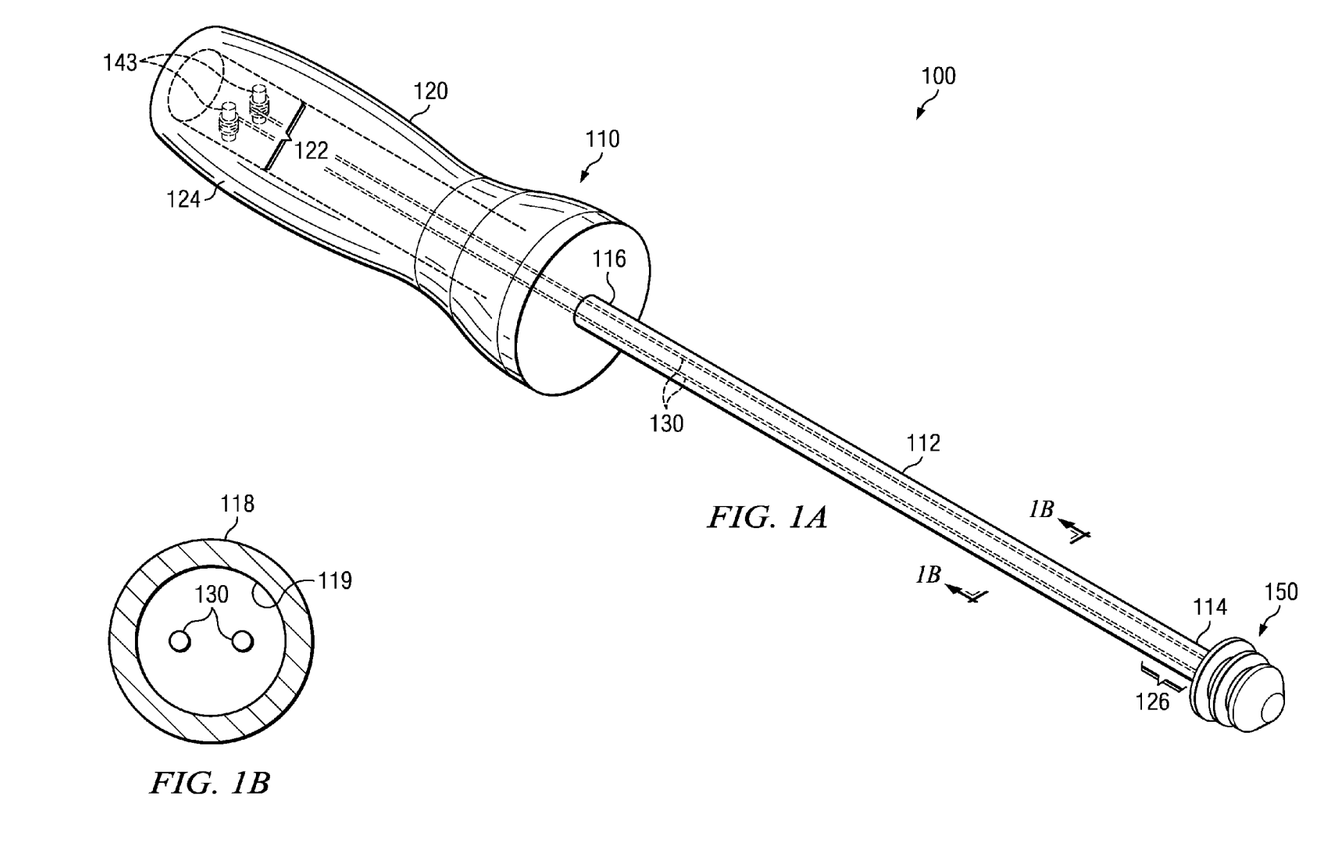
FIG. 1A shows a placement assembly according to the teachings of the present disclosure.
FIG. 1B shows a cross section of a placement assembly according to the teachings of the present disclosure.

FIG. 1A shows a placement assembly 100 according to the teachings of the present disclosure. Assembly 100 generally includes at least one graft pulley placement instrument 110, at least one surgical suture 130 (shown in phantom) and at least one graft pulley 150.

Instrument 110 includes a handle 120 and an elongate body 112; body 112 may be tubular. Elongate body 112 includes a distal end 114 and proximal end 116 to which instrument handle 120 is preferably connected. Handle 120 generally facilitates manipulation of instrument 110. In the present embodiment a suture securing portion 122 is formed within handle 120 or may alternatively be formed on handle surface 124. Securing portion 122 is preferably adapted to temporarily secure suture 130 until graft pulley 150 has been inserted. Suture securing portion 122 may include at least one post or tab 143 that suture 130 wraps around. In alternative embodiments securing portion 122 may include grooves or hooks to secure suture 130. Handle 120 may include a clam shell type recess or slot (not expressly shown) to access the suture 130 once pulley 150 is in place. The present embodiment shows a barrel type handle 120; however the present invention may be employed with any suitable handle shape of configuration such as T-grip type handle.

Instrument elongate body 112 may generally include a smooth outer surface 118 and an inner luminal surface 119 as shown in FIG. 1B. Elongate body distal end 114 may also include a connecting portion 126, adapted to removably connect with graft pulley 150. As shown in FIGS. 1A and 1B, suture 130 may extend from graft pulley 150 along inner lumen 119 to instrument handle 120 and instrument handle securing portion 122. Suture 130 may be contained within elongate body 112. In alternative embodiments not shown here, suture 130 may extend along a groove positioned longitudinally along elongate body outer surface 118 or juxtaposition upon the outside surface 118 of elongate body. Alternative embodiments with the suture 130 on the outside of the elongate body may be preferable should the surgeon wish to pre-attach the ligament before pulley 150 insertion.

Figure 2:
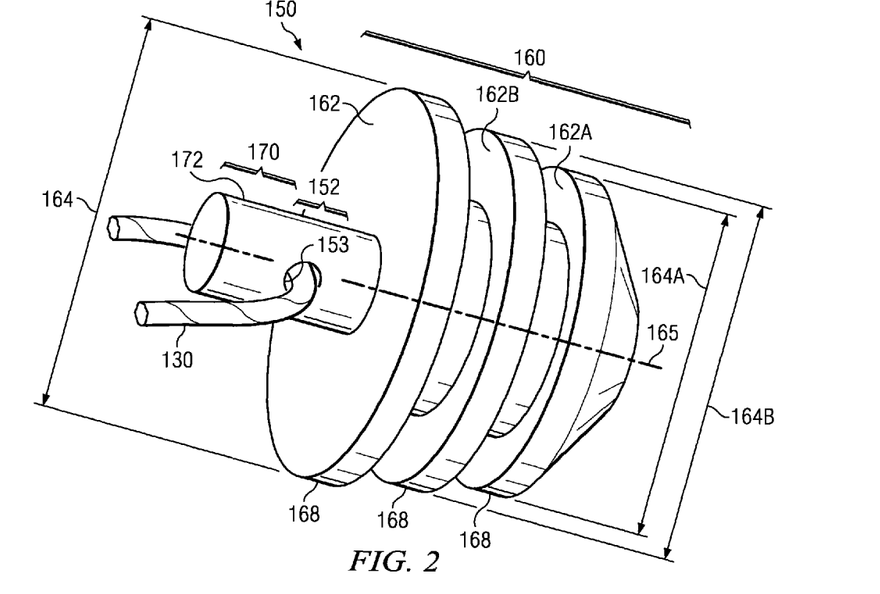
FIG. 2 shows a graft pulley according to the teachings of the present disclosure.

Graft pulley 150 is shown in more detail in FIG. 2. Graft pulley 150 generally includes a pulley portion 152, a bone anchoring portion 160 and an instrument attachment portion 170. Graft pulley 150 is preferably constructed from an implant grade material and portions of graft pulley 150 may also be constructed from a radiopaque material to aid in visualization using imaging techniques such as fluoroscopy or radiography. Bone anchoring portion 160 may comprise at least one flexible wing 162 adapted to secure graft pulley 150 within a bone tunnel. In the present embodiment wing 162 is a substantially flat, circular disc. In alternative embodiments, wing 162 may be non-cylindrical and/or non-circular in shape and may be any shape suitable for anchoring techniques described herein. In alternative embodiments, wing 162 may have a uniform thickness, as shown in the present embodiment, or may have a variable thickness. Each wing 162 has a non-flexed cross sectional dimension 164, measured when wing 162 is in a neutral relaxed position and each wing 162, 162A and 162B may have a different cross sectional dimension 164, 164A and 164B from any other wing, to account for variation in bone tunnel size or shape and to facilitate insertion into a bone tunnel. Alternatively, more or fewer flexible wings 142 may be provided. In some alternate embodiments, flexible wings 142 may have a substantially uniform cross sectional dimension 164. Three flexible wings 162, 162A and 162B are shown in FIG. 2, each with differing cross sectional dimensions 164. As shown in FIG. 2, each wing 162, 162A and 162B is progressively smaller cross sectional dimension 164, 164A and 164B. As shown, a first wing 162A includes a cross sectional dimension 164A and a second wing 162B includes a cross sectional dimension 164B. In the present embodiment first cross sectional dimension 164A is smaller than second cross sectional dimension 164B. In alternative embodiments wing 162 may not form a continuous disc or other shape, but may include slots or gaps in wing 162 (not expressly shown). In the present embodiment wing 162 is shown positioned approximately perpendicular to longitudinal axis 165.

Wing 162 may be formed so as to preferably flex during insertion into a bone tunnel and resist flex and wedge into the bone tunnel if pulley 150 is pulled in a direction approximately opposing the direction of insertion. This flexing occurs as a result of inserting pulley 150 into the tunnel, as they inherently bend downstream as a result of insertion, so as to fit within tunnel. In the embodiment shown in FIG. 2, at least one wing cross sectional dimension 164 is designed to be larger than the intended bone tunnel diameter (described in a later figure). Wings 162, 162A and 162B may preferably be constructed from a flexible material such as high density polyethylene.

In some embodiments, wing edges 168 may be formed to facilitate fixation of pulley 150. For example, wing edges 168 may be formed with a surface texture (not expressly shown) and/or a high friction coating may be disposed on wing edge 168 to increase friction between wing edge 168 and the bone tunnel wall and thereby increase the relative fixation strength or so-called pull-out strength of pulley 150 after implantation. However, the expected load on pulley 150 during ligament insertion and positioning may be relatively small as pulley 150 may be used primarily for positioning of a ligament within the bone tunnel and other surgical instruments may assist in positioning. Following the positioning of the ligament, the ligament may be held in tension, thereby exerting a force on pulley 150, as a suitable fixation device, such as a cannulated screw or expandable device, is inserted within the bone tunnel and secure the ligament therein.

Pulley portion 152 includes at least one opening or aperture 153 sized to receive surgical suture 130. Pulley portion aperture 153 is sized so as to allow standard sized surgical suture 130 to easily slide through said aperture 153 and may be oriented approximately perpendicular to longitudinal axis 165. Pulley portion 152 may be made from substantially low friction materials such as polyolefin to allow suture 130 to easily slide through aperture 153. In alternative embodiments, not shown here, aperture may be a channel or tunnel that extends into pulley 150 and pulley portion 152 may be fully or partially recessed within bone anchoring portion 160.

Graft pulley instrument attachment portion 170 is generally adapted to removably attach to an instrument (not shown here) used to insert graft pulley 150 within a bone tunnel. Shown here, graft attachment portion 170 is a shaft 172. An instrument with a hollow lumen (not shown here) may then removably slide over said shaft 172 to manipulate pulley 150 into a bone tunnel. An instrument may then slide off shaft 172 to disengage. Shaft 172 may be substantially circular in shape. Alternate embodiments may include a substantially non circular shaft 172, which may aid in pulley 150 orientation or rotation if needed. Shaft 172 may preferably be sized to insert the pulley 150 into the tunnel but easily slide off once retracted. In alternative embodiment, suture 130 may also cause a frictional or interference fit between the shaft 172, suture 130 and the instrument lumen. In alternative embodiments the shaft 172 may be adapted to selectively disengage from pulley 150, via release mechanisms or friction fits, not shown here.

Figure 3:
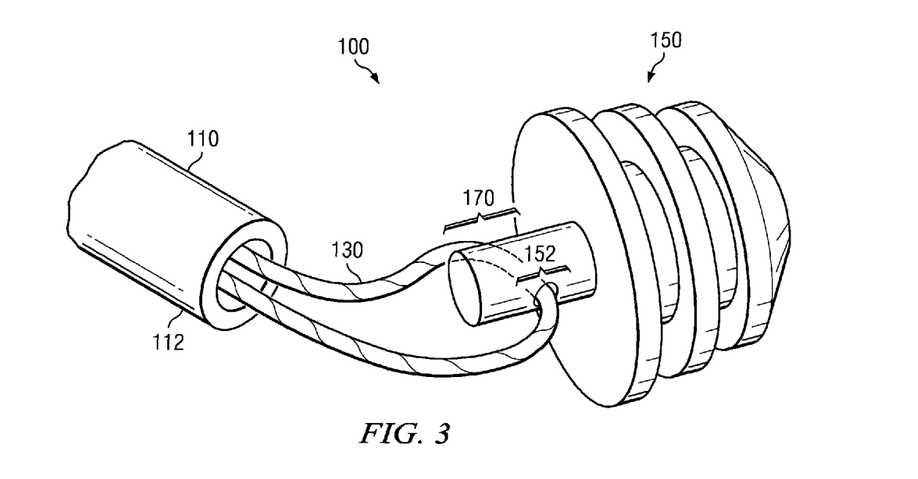
FIG. 3 shows a partial view of a placement assembly, disassembled to show the suture, according to the teachings of the present disclosure.

FIG. 3 shows a partial view of a placement assembly 100, shown with instrument 110 disconnected from anchor 150. Assembly 100 generally includes a graft pulley 150 having a pulley portion 152 and instrument attachment portion 170, surgical suture 130 and placement instrument 110. Shown in FIG. 3 is an embodiment with suture 130 assembled within instrument elongate body 112. Suture 130 is shown assembled with pulley portion 152. Instrument attachment portion 170 is adapted to removably engage with distal end 114 of elongate body 112.

Figure 4A:
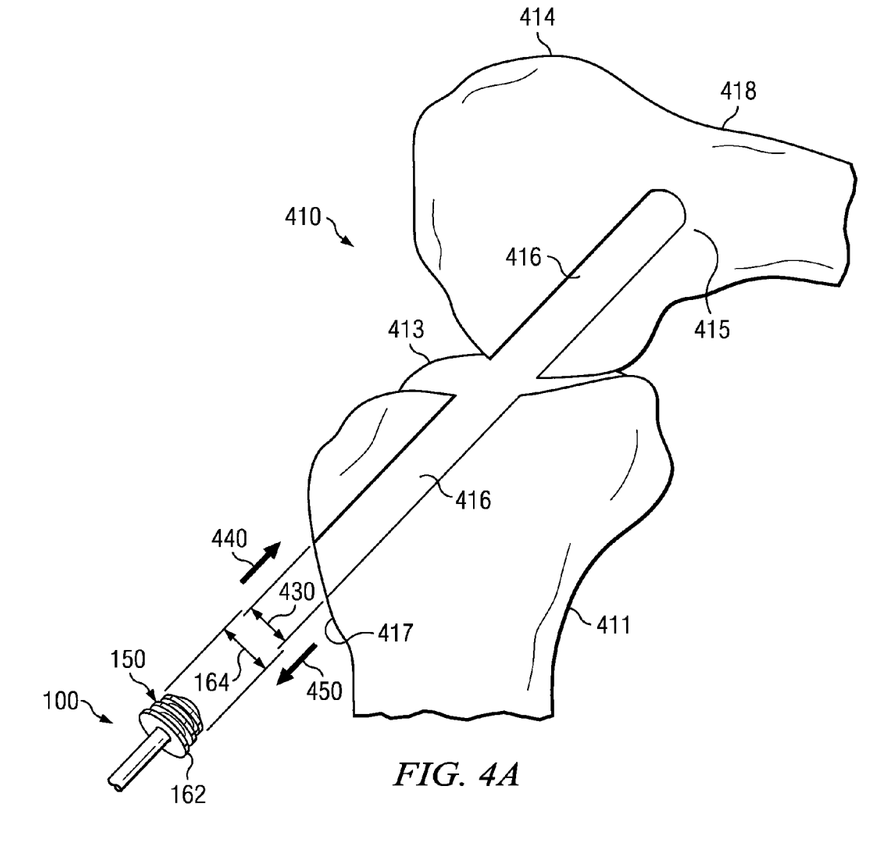
FIG. 4A shows a placement assembly before insertion into a bone tunnel according to the teachings of the present disclosure.

FIG. 4A shows a placement assembly 100 ready to be inserted into a patient's knee 410. Knee 410 is shown with tibia 411 approximately ninety degrees with respect to femur 414. A bone tunnel 416 has been formed in an upper anterior portion 417 of the tibia 411, extending into a distal end 415 of femur 414 through knee capsule 413. In the present embodiment, the distal end of the femur capsule 418 may not be punctured, that is, bone tunnel 416 extends only partially into femur 414. In some embodiments, bone tunnel 416 may include a guide or pilot hole that does extend through the end of femur capsule 418. Bone tunnel 416 has a bone tunnel diameter 430. In alternate embodiments, bone tunnel diameter may not be constant along the length the of bone tunnel 416.

Graft pulley 150 is shown with at least one wing 162 that has a non-flexed cross sectional dimension 164 that is larger than bone tunnel diameter 430. During the insertion of assembly 100 in first direction 440, at least one wing 162 may preferably flex in second direction 450 to allow for slideable insertion of assembly down bone tunnel. Bone tunnel diameters 430 may vary in size depending on the tool a surgeon chooses to drill said tunnel. Some exemplary diameters 430 vary from 7 mm to 12 mm and therefore a variety of wing cross sectional dimensions 164 may also be provided. Wing cross sectional dimensions 164 may be approximately between 1 mm and 4 mm greater than the bone tunnel diameter 430 and more preferably be approximately 1-2 mm greater than the respective bone tunnel diameter 430. Therefore, for example, for a tunnel diameter 430 that is approximately 10 mm, a pulley cross sectional dimension 164 may preferably be no larger than approximately 12 mm at any point on at least one wing 162. This cross sectional dimension 164 may depend on material properties such as elastic modulus and shape, thickness and size of the wing 162.

Figure 4B:
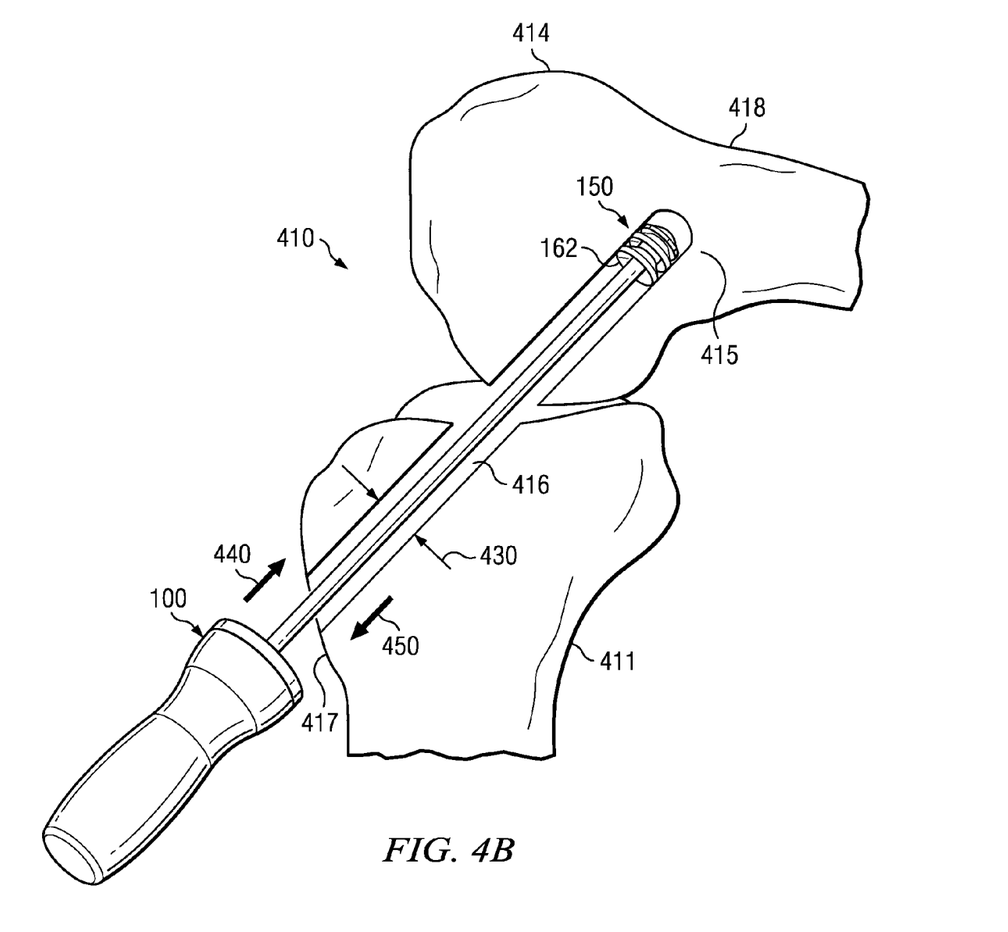
FIG. 4B shows a placement assembly during insertion into a bone tunnel according to the teachings of the present disclosure.

Placement assembly 100 is then preferably inserted into bone tunnel 416 in first direction 440 as shown in FIG. 4B and pulley 150 is shown with at least one wing 162 that is flexed to facilitate insertion. As pulley 150 enter bone tunnel 416, wing 162 preferably flexes in second direction 450 to conform to tunnel diameter 430, which is smaller than wing non flexed cross sectional dimension 164. Thereafter, wing 162 will resist any attempt to withdraw or retract pulley 150 in second direction 450. This resistance provided by wing 162 is preferable sufficient to position a ligament graft as described below. In a preferred embodiment, wing 162 will preferably not flip or flex to first direction 440 and will essentially wedge graft pulley 150 in place within the tunnel. However, if pulley 150 is not considered deep enough in the tunnel 416 at any time, pulley 150 may be easily repositioned further along the first direction, into the tunnel. Instrument may be re-engaged in order to reposition pulley 150, if instrument has been disengaged. In the present embodiment pulley 150 will preferably not burrow or dig into bone tunnel 416 during use.

Figure 5A:
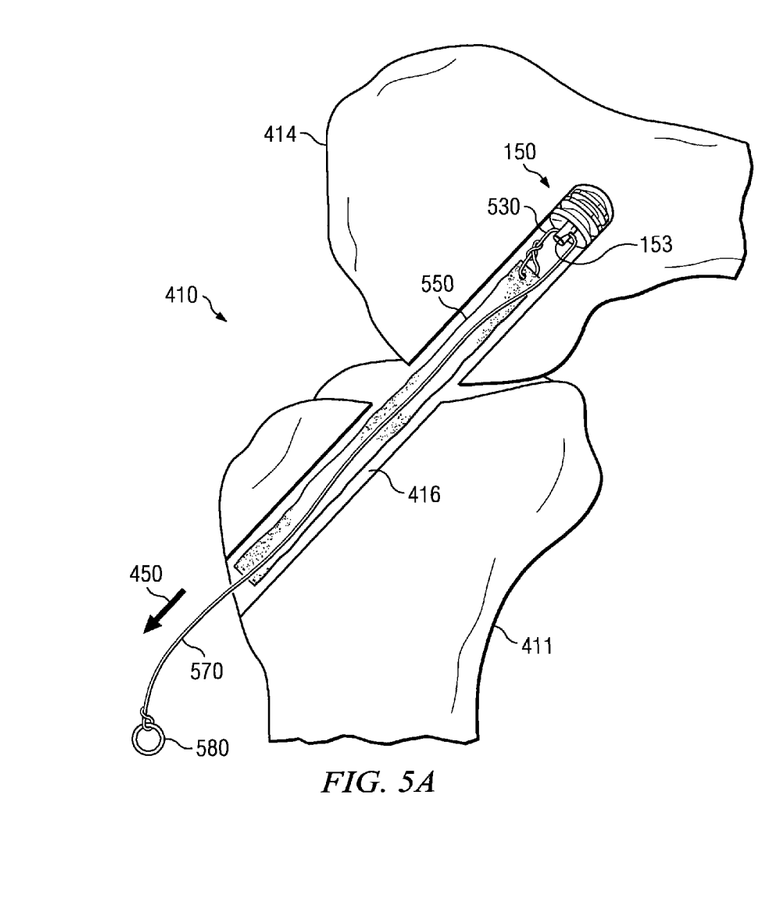
FIGS. 5A, 5B and 5C are representations of a graft pulley in place and a ligament graft attached with alternative embodiments of suture routing.

FIG. 5A shows a ligament graft 550 being positioned within bone tunnel 416. Similar to FIG. 4, knee 410 is shown with tibia 411 and femur 414 in a ninety degree position. Graft pulley 150 is shown firmly fixed within bone tunnel 416. Graft 550 is shown attached to a suture first end 530. A suture needle (not shown) may be used to attach ligament 550 to suture 530. A suture second end 570 may then be pulled in second direction 450 out of tunnel 416, to position graft 550 in place within tunnel 416. Suture second end 570 may also include a stop button or stop ring 580 adapted to prevent suture second end 570 from traveling into bone tunnel 416 and potentially through pulley aperture 153. Once ligament 550 is in place ligament, suture end 570 may be cut as close to the pulley as possible. Alternately suture may left within the tunnel 416 and may be made of a suitably absorbable material. Ligament 550 may be further anchored into place using traditional anchors and instruments for ligament repair as are well known to those of skill in the art.

Figure 5B:
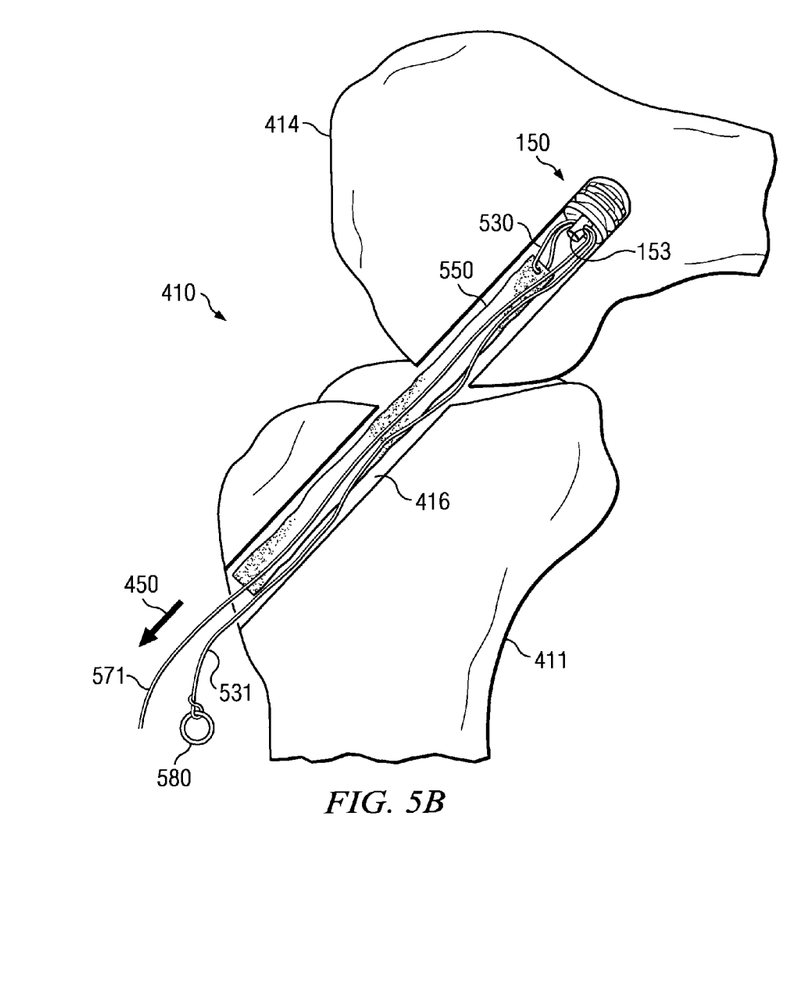

FIG. 5B shows a ligament graft 550 being positioned within bone tunnel 416 using an alternative suture routing. This alternate routing may allow the surgeon the ability to remove the suture 530 from the tunnel 416, if desired. Similar to FIG. 4, knee 410 is shown with tibia 411 and femur 414 in a ninety degree position. Graft pulley 150 is shown firmly fixed within bone tunnel 416. Graft 550 is shown with suture 530 looped through ligament 550 and then two suture ends 531 and 571 routed through pulley aperture 153 together, in the same direction. A suture needle (not shown) may be used to attach ligament 550 to suture 530, and for this alternate suture routing, suture may be attached to ligament 550 and routed through pulley 150, before placement of pulley 150 within bone tunnel 416. Alternatively, a suture shuttle (not expressly shown) may be integral to the insertion instrument to route the suture according to FIG. 5B. Suture ends 531 and 571 may then be pulled, in tandem, in second direction 450 out of tunnel 416, to position graft 550 in place within tunnel 416. At least one of suture ends 531 or 571, may also include a stop button or stop ring 580, adapted to prevent suture second end 571 from traveling into bone tunnel 416 and potentially inadvertently through pulley aperture 153. Once ligament 550 is in place, suture end 531 may then be pulled in second direction 450 so as to withdraw suture 530 completely from pulley 150 and ligament 550 and out of tunnel 416. Ligament 550 may then be further anchored into place using traditional anchors and instruments for ligament repair as are known to those of skill in the art.

Figure 5C:
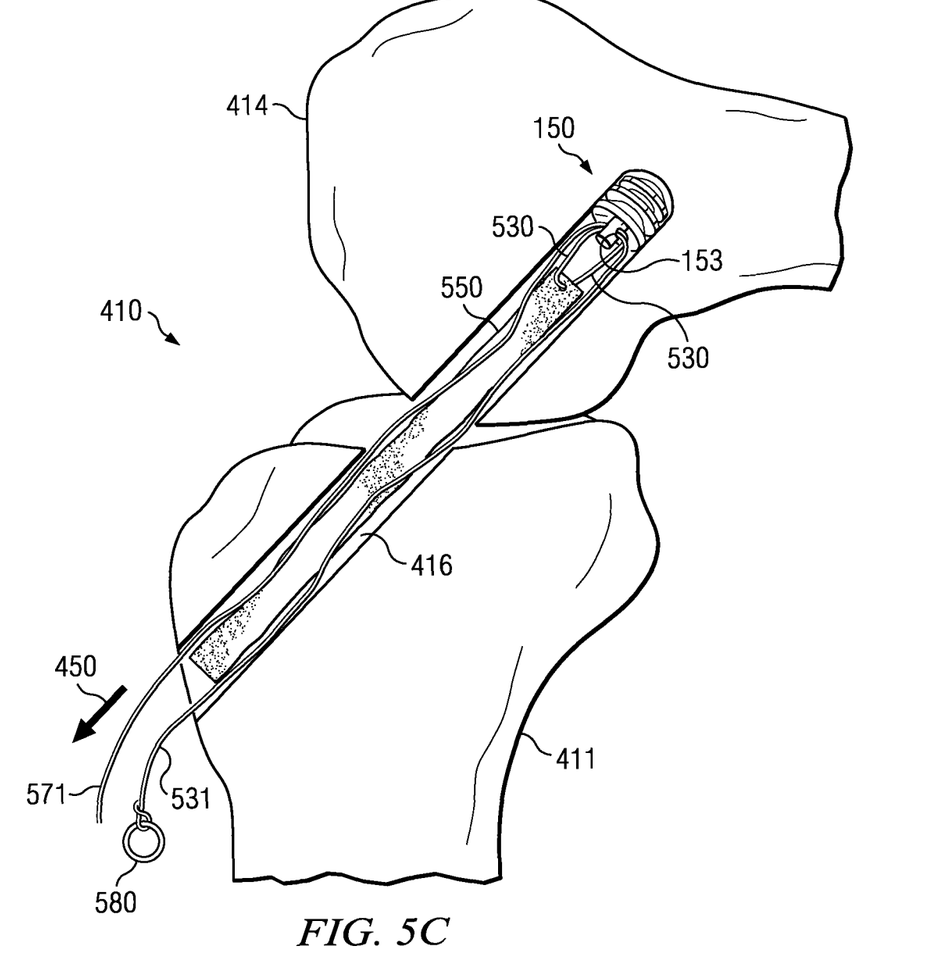

FIG. 5C shows a ligament graft 550 being positioned within bone tunnel 416 using an alternative routing of a suture, similar in spirit to FIG. 5B. This alternate routing may allow the surgeon the ability to remove the suture 530 from the tunnel 416. Similar to FIG. 4, knee 410 is shown with tibia 411 and femur 414 in a ninety degree position. Graft pulley 150 is shown firmly fixed within bone tunnel 416. Graft 550 is shown with suture 530 attached to ligament 550 and then two suture ends 531 and 571 are routed through pulley aperture 153. The two suture ends 531 and 571 are routed through the graft pulley 150 in opposing directions. A suture needle (not shown) may be used to attach ligament 550 to suture 530, and for this alternate suture routing, suture may need to be attached to ligament 550 and pulley 150, before placement of pulley 150. Alternatively, a suture shuttle (not shown) may be integral to the insertion instrument to route the suture according to FIG. 5B. Suture ends 531 and 571 may then be pulled, in tandem, in second direction 450 out of tunnel 416, to position graft 550 in place within tunnel 416. At least one of suture ends 531 or 571, may also include a stop button or stop ring 580 adapted to prevent suture second end 570 from traveling into bone tunnel 416 and potentially inadvertently through pulley aperture 153. Once ligament 550 is in place ligament, suture end 531 may then be pulled in second direction 450 so as to withdraw suture 530 from pulley 150 and ligament 550, and subsequently out of tunnel 416. Ligament may then be further anchored into place with using traditional anchors and instruments for ligament repair as are known to those of skill in the art.

Figure 6A:
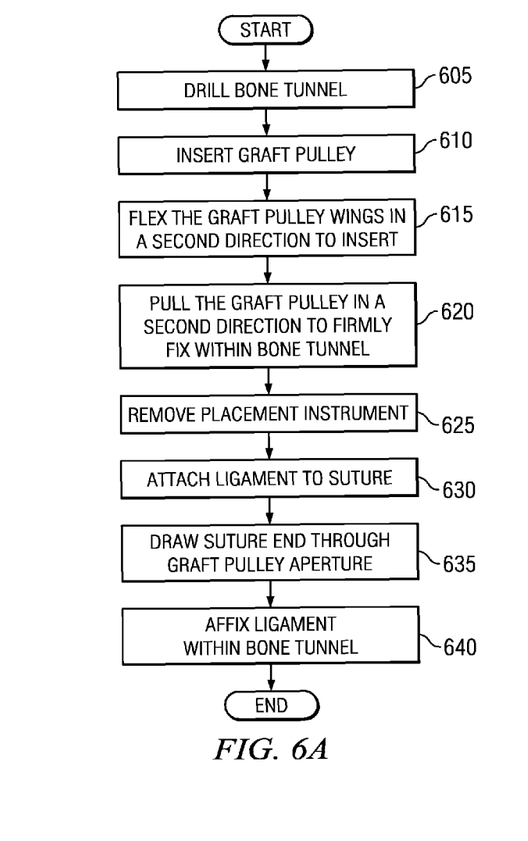
FIGS. 6A and 6B show flow diagrams of methods of using the present invention in a medical procedure, according to the teachings of the present disclosure.

A method of performing a portion of a medical procedure using a graft pulley is shown in FIG. 6A. A knee joint is first positioned at a ninety degree angle and a bone tunnel is drilled 605 from an upper anterior portion of a tibia through a knee capsule and partially within a distal end of a femur without penetration into a lateral femoral cortex. A graft pulley is then inserted 610, using a placement instrument. Graft pulley includes a pulley portion sized to receive surgical suture and a bone anchoring portion; the anchoring portion includes one or more flexible wings adapted to fix the graft pulley within the bone tunnel. The wings may be flexed 615 in a second direction as the graft pulley is inserted into the bone tunnel in the first direction. The graft pulley may then be pulled in a second direction 620 to firmly fix graft pulley within bone tunnel. Placement instrument may then be detached and withdrawn 625, leaving graft pulley in place.

Thereafter a ligament graft may be provided and attached 630 to surgical suture. Suture end may then be drawn 635 through graft pulley aperture in order to position graft within a bone tunnel. If the pulley is not deemed far enough along the tunnel, at any time, an additional step may be added, further inserting the pulley into the bone tunnel before the step of detaching the placement instrument. Alternatively, the placement instrument may be re-engaged.

The ligament may then be fixed in position within the bone tunnel 640. Fixing the ligament more permanently to the tunnel wall is achieved using a large variety of bone anchors that are well known to one skilled in the art. The suture may be left within the tunnel, or may be cut during the step of fixing the ligament in place, leaving only a portion of suture in-situ. Alternatively, the surgeon may chose to cut the suture before the step of fixing the ligament in position.

Figure 6B:
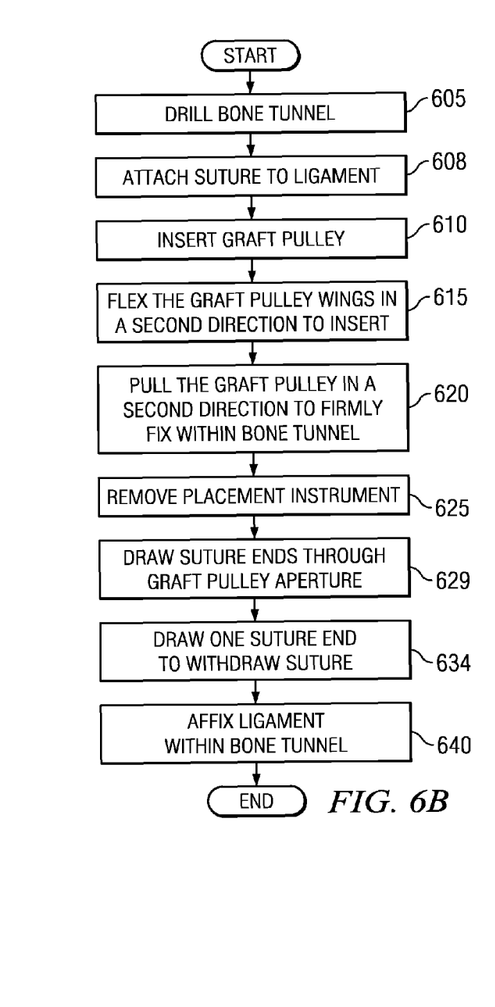

An alternate method of performing a portion of a medical procedure using a graft pulley is shown in FIG. 6B. A knee joint is first positioned at a ninety degree angle and a bone tunnel is drilled 605 from an upper anterior portion of a tibia through a knee capsule and partially within a distal end of a femur without penetration into a lateral femoral cortex. A suture may then be attached 608 to a ligament to preassemble the suture and ligament before pulley insertion. A suture may also be inserted through a pulley portion of a graft pulley sized to receive surgical suture. A graft pulley is then inserted 610, using a placement instrument. Graft pulley includes a pulley portion and a bone anchoring portion; the anchoring portion includes one or more flexible wings adapted to fix the graft pulley within the bone tunnel. The wings may be flexed 615 in a second direction as the graft pulley is inserted into the bone tunnel in the first direction. The graft pulley may then be pulled in a second direction 620 to firmly fix graft pulley within bone tunnel. Placement instrument may then be detached and withdrawn 625, leaving graft pulley in place.

Both suture ends may then be drawn 629 through graft pulley aperture, in order to position graft within a bone tunnel. Once ligament is in position, one suture end may then be drawn 634 so as to withdraw the suture from the tunnel. The ligament may then be fixed in position within the bone tunnel 640.

Figure 7A:
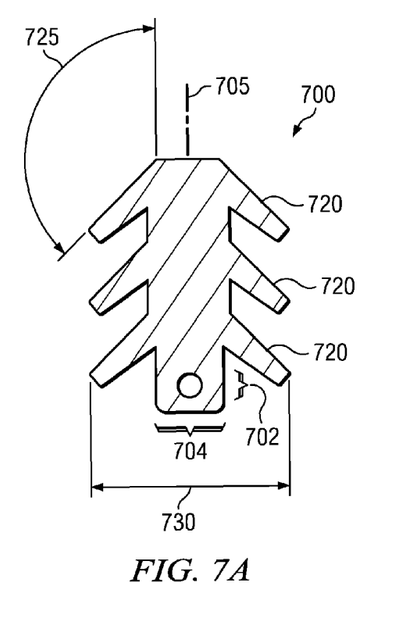
FIGS. 7A and 7B show longitudinal cross sectional views of alternative graft pulley embodiments.

FIG. 7A shows a longitudinal cross section of an alternative embodiment of a graft pulley 700. Graft pulley 700 is similar in spirit to the previous pulley described and includes a pulley portion 702, attachment portion 704, longitudinal axis 705 and at least one wing 720. At least one wing 720 is formed at an angle 725 to longitudinal axis 705. Angle 725 may improve the ease of pulley 700 insertion into a bone tunnel. Wing non-flexed outer cross sectional dimension 730 may be substantially larger than an intended bone tunnel diameter to make graft pulley 700 wedge within the tunnel when a retraction force is applied. Wing 720 may be circular or non-circular.

Figure 7B:
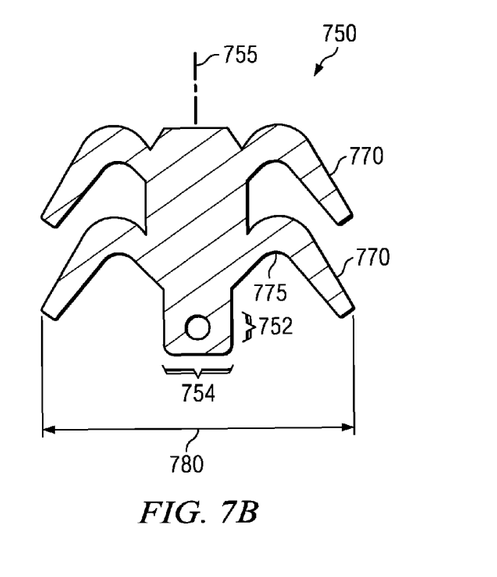

FIG. 7B shows a longitudinal cross section of an alternative embodiment of a graft pulley 750. Pulley 750 is similar in spirit to previous pulley described and includes a pulley portion 752, attachment portion 754, longitudinal axis 755 and at least one wing 770. At least one wing 770 is formed in the shape of a hook 775. Hook 775 may improve the ease of pulley 750 insertion into a bone tunnel and provide for improved affixation strength. Wing non flexed outer cross sectional dimension 780 may be larger than an intended bone tunnel diameter to make pulley 750 wedge within a bone tunnel. Wing 770 may be circular or non-circular.

Figure 8:
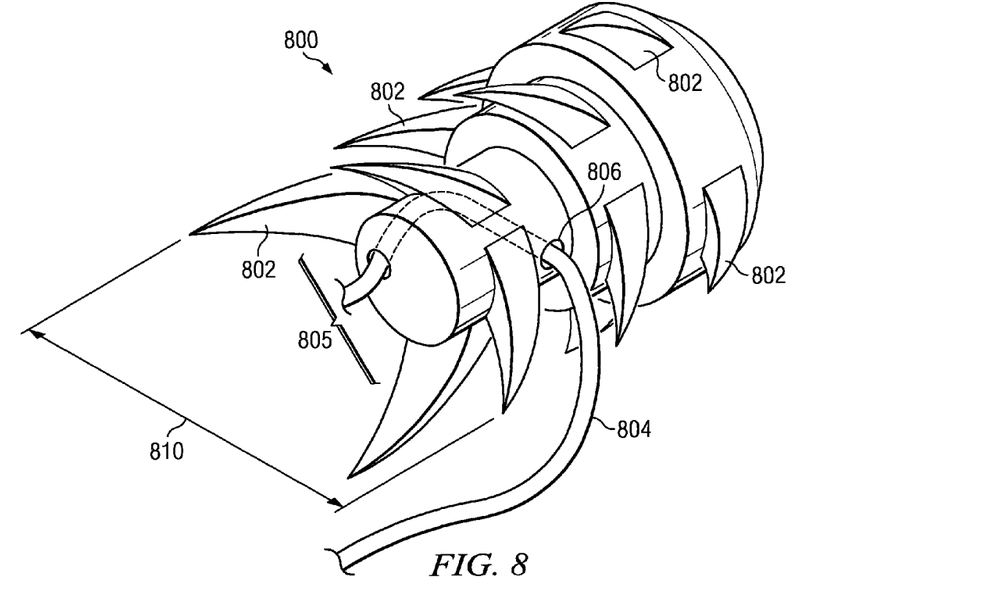
FIG. 8 shows an alternative embodiment of a graft pulley.

FIG. 8 shows a view of an alternative embodiment of a graft pulley 800. Pulley is similar in spirit to pulleys previously described and includes at least one radially extending flexible fin or hook 802 formed to firmly fix the pulley 800 within a bone tunnel (not shown here). A series of hooks or fins 802 may be formed in rows (as shown) or fins 802 may be arranged in a helix or randomly disposed along pulley 800. Similar to previous figures, the non-flexed cross sectional dimension 810 may preferably be selected to be larger than a respective bone tunnel diameter (not shown here). At least one fin 802 may flex upon pulley 800 insertion into a bone tunnel in a first direction and then resist flex when pulled in a second direction out of said bone tunnel, effectively affixing pulley 800 within bone tunnel. This pulley 800 embodiment may adapt better to uneven bone tunnel shapes.

Pulley 800 also shows a pulley portion 805 including a suture aperture 806 in a channel shape, located inside pulley 800. Suture 804 is shown threaded along suture channel 806 and is similar in spirit to previous pulley portions described. This embodiment may show improved durability over previous embodiments described as it is internal to the body of the pulley 800. Alternate embodiments (not shown here) may include a pulley with an anchoring portion comprising at least two fins or hooks, legs or wings. These fins etc. may have a cross sectional dimension smaller than that of a bone tunnel and with heat or mechanical activation, at least one fin may recover to a position that increases the cross sectional dimension to a size larger or equal to a bone tunnel diameter, thus wedging the pulley within the bone tunnel.

Although only a few embodiments of the present invention have been described, it should be understood that the present invention may be embodied in many other specific forms without departing from the spirit or the scope of the present invention. Therefore, the present examples are to be considered as illustrative and not restrictive, and the invention is not to be limited to the details given herein, but may be modified within the scope of the appended claims.

What is claimed is:

1. A placement assembly for positioning a ligament graft within a selected bone tunnel comprising:
    a graft pulley, having a pulley portion and a bone anchoring portion;
    the pulley portion having an aperture sized to receive a surgical suture;
    the bone anchoring portion operable to selectively fix the graft pulley within a bone tunnel, the anchoring portion having at least one flexible wing, the flexible wing having a radially extending diameter larger than a diameter of the selected bone tunnel, wherein the at least one flexible wing is operable to flex from a first position wherein the at least one flexible wing is substantially flat to a second position wherein the at least one flexible wing is convex relative to a direction of insertion, and wherein the at least one flexible wing is sized so as to be restricted from returning to the first position while inserted in the bone tunnel; and
    a graft pulley placement instrument having an elongate body and a handle;
    the elongate body adapted to insert the graft pulley into the selected bone tunnel.

2. The placement assembly of claim 1 wherein at least one wing is sized so as to wedge into the bone tunnel and remain in the second position when the graft pulley is pulled in a second direction via the surgical suture wherein the second direction is substantially opposite the direction of insertion.

3. The placement assembly of claim 1 wherein the graft pulley is adapted to allow motion in a first direction and resist movement along a second direction, both during and after insertion, where the first direction is substantially opposite the second direction.

4. The placement assembly of claim 1 wherein the graft pulley placement instrument handle comprises a suture securing portion, adapted to manage the surgical suture.

5. The placement assembly of claim 1 wherein the suture comprises a stop button adapted to prevent the suture from traveling through the anchor pulley aperture.

6. The placement assembly of claim 1 wherein a needle is removably attached to the suture for attaching the suture to a ligament graft.

7. The placement assembly of claim 1 wherein the graft pulley includes an attachment portion and the placement instrument includes a connecting portion, adapted to removably connect with the pulley attachment portion.

8. A graft pulley for positioning a ligament graft within a selected bone tunnel comprising:
    a pulley portion having an aperture, sized to receive a surgical suture; and
    a bone anchoring portion having at least one flexible wing extending radially from a graft pulley longitudinal axis, the at least one wing adapted to selectively fix the graft pulley within a bone tunnel, wherein the at least one wing has a non-flexed cross sectional dimension larger than a diameter of the selected bone tunnel, and wherein the at least one wing is operable to irreversibly flex to a flexed position, during insertion of the graft pulley into the selected bone tunnel in a first direction such that the flexed position is characterized as convex relative to the first direction.

9. The graft pulley of claim 8 further comprising an attachment portion adapted to removably connect with a graft pulley placement instrument.

10. The graft pulley of claim 8 wherein the graft pulley is adapted to allow motion in the first direction and resist movement along a second direction at all times, and the first direction is substantially opposite the second direction.

11. The graft pulley of claim 8 wherein at least one wing is disc shaped and disposed approximately concentric with a longitudinal axis of the pulley.

12. The graft pulley of claim 8 wherein the pulley has a longitudinal axis and wherein at least one wing is formed substantially perpendicular to said longitudinal axis.

13. The graft pulley of claim 8 wherein the at least one wing extends at an angle to the longitudinal axis.

14. The graft pulley of claim 8 wherein the at least one wing comprises a hook radiating from said pulley longitudinal axis.

15. The graft pulley of claim 8 wherein the anchoring portion comprises at least one flexible fin radiating from said pulley longitudinal axis.

16. The graft pulley of claim 8 wherein the graft pulley fixes within the bone tunnel without trauma to the bone tunnel.

17. The graft pulley of claim 8 wherein the pulley portion comprises a low friction material.

18. The graft pulley of claim 17 wherein the pulley portion comprises a polyolefin.

19. The graft pulley of claim 8 wherein a portion of the graft pulley comprises a radiopaque material.

20. The graft pulley of claim 8 wherein the at least one wing comprises a first wing having a first cross sectional dimension and a second wing with a second cross sectional dimension.

* * * * *